(12) United States Patent
Mosebach et al.

(10) Patent No.: US 10,279,130 B2
(45) Date of Patent: May 7, 2019

(54) MEDICAMENT DELIVERY DEVICE WITH MEDICAMENT DELIVERY INITIATION INDICATOR

(71) Applicant: SANOFI-AVENTIS DEUTSCHLAND GMBH, Frankfurt am Main (DE)

(72) Inventors: Carsten Mosebach, Frankfurt am Main (DE); Stefan Wendland, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 11 days.

(21) Appl. No.: 14/433,333

(22) PCT Filed: Oct. 1, 2013

(86) PCT No.: PCT/EP2013/070463
§ 371 (c)(1),
(2) Date: Apr. 2, 2015

(87) PCT Pub. No.: WO2014/053496
PCT Pub. Date: Apr. 10, 2014

(65) Prior Publication Data
US 2015/0258286 A1    Sep. 17, 2015

(30) Foreign Application Priority Data
Oct. 4, 2012    (EP) ..................................... 12187308

(51) Int. Cl.
*A61M 5/50*    (2006.01)
*A61M 5/32*    (2006.01)
*A61M 5/315*   (2006.01)

(52) U.S. Cl.
CPC ........ *A61M 5/5086* (2013.01); *A61M 5/3157* (2013.01); *A61M 5/3202* (2013.01);
(Continued)

(58) Field of Classification Search
CPC .... A61M 5/3157; A61M 5/32; A61M 5/3202; A61M 5/3243; A61M 5/3257;
(Continued)

(56) References Cited

U.S. PATENT DOCUMENTS

2010/0268171 A1* 10/2010 Moller .............. A61M 5/31551
604/246
2011/0092915 A1*  4/2011 Olson ................. A61M 5/2033
604/198

FOREIGN PATENT DOCUMENTS

JP    2012/5132720    6/2012
WO   WO 2010/072702   7/2010
(Continued)

OTHER PUBLICATIONS

European Search Report in European Application No. 12187308.7, dated Mar. 18, 2013, 6 pages.
(Continued)

*Primary Examiner* — Nathan R Price
*Assistant Examiner* — Justin L Zamory
(74) *Attorney, Agent, or Firm* — Fish & Richardson P.C.

(57) ABSTRACT

Described is a medicament delivery device (100, 200) comprising a case (105, 205) adapted to hold a container with a medicament and a needle (300), a needle sleeve (120, 220) telescopically coupled to the case (105, 205) and having an extended position relative to the case (105, 205) in which the needle (300) is covered and a retracted position relative to the case (105, 205) in which the needle (300) is exposed, and a delivery initiation indicator providing a visual feedback of an initiation of a delivery of the medicament when the needle sleeve (120, 220) is in the retracted position.

16 Claims, 5 Drawing Sheets

(52) U.S. Cl.
CPC .......... *A61M 5/326* (2013.01); *A61M 5/3257* (2013.01); *A61M 2205/583* (2013.01)

(58) Field of Classification Search
CPC ...... A61M 5/326; A61M 5/50; A61M 5/5086; A61M 2005/2013; A61M 2005/208; A61M 2005/3263; A61M 2005/3267; A61M 2005/3268; A61M 2205/583
USPC ................. 604/111, 137, 187, 192, 193, 198
See application file for complete search history.

(56) References Cited

FOREIGN PATENT DOCUMENTS

| WO | WO 2011/095486 | 8/2011 |
|----|----------------|--------|
| WO | WO 2012/072559 | 6/2012 |
| WO | WO 2012/072562 | 6/2012 |
| WO | WO 2012/072563 | 6/2012 |

OTHER PUBLICATIONS

International Preliminary Report on Patentability and Written Opinion in International Application No. PCT/EP2013/070463, dated Apr. 7, 2015, 5 pages.
International Search Report in International Application No. PCT/EP2013/070463, dated Jan. 14, 2014, 4 pages.
Japanese Office Action in Application No. 2015-534989, dated Jun. 27, 2017, 6 pages.

* cited by examiner

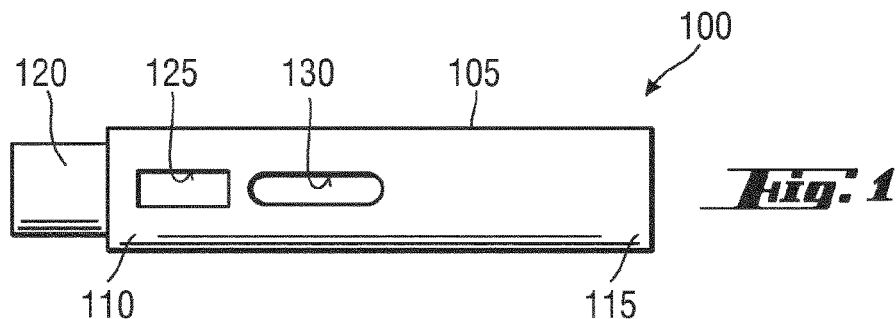
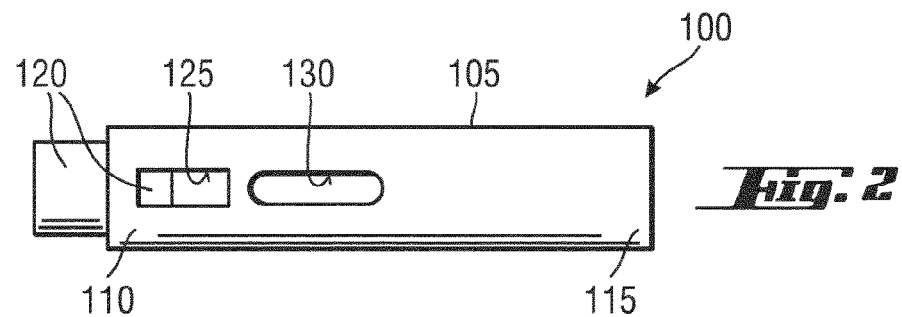
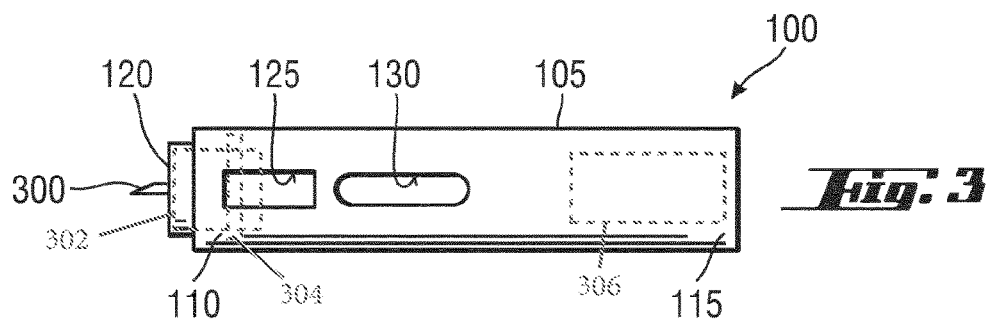
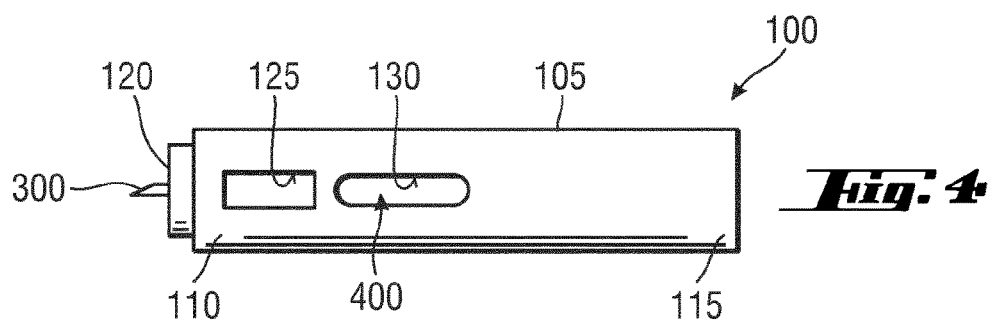
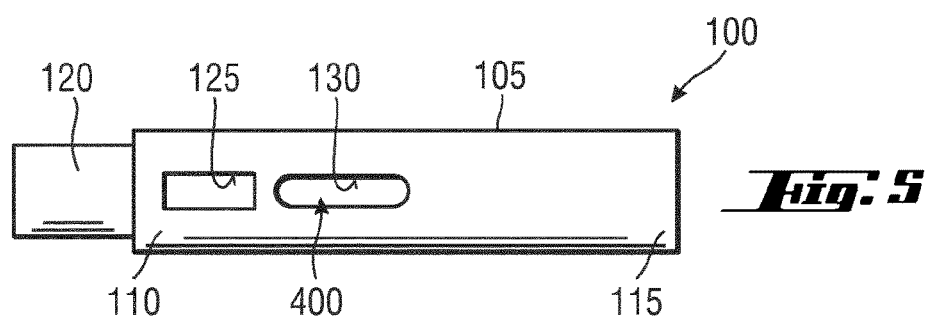

MEDICAMENT DELIVERY DEVICE WITH MEDICAMENT DELIVERY INITIATION INDICATOR

This application is a 371 U.S. National Application of PCT/EP2013/070463, filed on Oct. 1, 2013, which claims priority to European Patent Application Nos. 12187308.7, filed on Oct. 4, 2012, the entire contents of which are incorporated herein by reference.

TECHNICAL FIELD

The invention relates to medicament delivery device with a medicament delivery initiation indicator.

BACKGROUND OF THE INVENTION

Administering an injection is a process which presents a number of risks and challenges for users and healthcare professionals, both mental and physical. Injection devices typically fall into two categories—manual devices and autoinjectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

Conventional delivery devices may also have limited feedback mechanisms. For example, some conventional delivery devices may only provide an audible feedback when an injection is complete. Thus, a patient may be startled when he/she feels a needle insertion or pressure associated with injection of a medicament if there is no warning. In this case, the patient may move or react during needle insertion or medicament delivery which may lead to injury, pain, or incorrect dose delivery.

Thus, there remains a need for an improved medicament delivery device with a medicament delivery initiation indicator.

SUMMARY OF THE INVENTION

It is an object of the present invention to provide an improved medicament delivery device with a medicament delivery initiation indicator.

In an exemplary embodiment, a medicament delivery device according to the present invention comprises a case adapted to hold a container with a medicament and a needle, a needle sleeve telescopically coupled to the case and having an extended position relative to the case in which the needle is covered and a retracted position relative to the case in which the needle is exposed, and a delivery initiation indicator providing a visual feedback of an initiation of a delivery of the medicament when the needle sleeve is in the retracted position.

In an exemplary embodiment, the medicament delivery device further comprises a spring biasing the needle sleeve in the extended position.

In an exemplary embodiment, the delivery initiation indicator is a window formed in the case which shows an increasing portion of the needle sleeve when the needle sleeve moves from the extended position to the retracted position. The increasing portion of the needle sleeve occupies a full visual area of the window when the needle sleeve is in the retracted position. The window has a shape of a rectangle, a droplet, a triangle or an arrow. An indicia is disposed on the window, on the case or on a portion of the needle sleeve that is visible through the window as the needle sleeve moves from the extended position to the retracted position. The indicia includes one or more words, symbols, numbers, colors or lines.

In an exemplary embodiment, the medicament delivery device further comprises a further window formed in the case which shows a portion of a plunger after delivery of the medicament.

In an exemplary embodiment, the medicament delivery device further comprises an interlock mechanism operably coupled to the needle sleeve and adapted to release the plunger to push a stopper in the container under a force of a compressed spring when the needle sleeve is in the retracted position.

In an exemplary embodiment, the delivery initiation indicator is an indicia formed on the needle sleeve. The indicia includes one or more words, symbols, numbers, colors or lines. The indicia is covered by the case when the needle sleeve is in the retracted position. The medicament delivery device further comprises a window formed in the case which shows a portion of a plunger after delivery of the medicament.

In an exemplary embodiment, the medicament delivery device further comprises a trigger button coupled to the case and operably coupled to the plunger, and an interlock mechanism operably coupled to the needle sleeve and the trigger button. When the needle sleeve is in the retracted position, the interlock mechanism releases the trigger button which can be pressed to release the plunger to push a stopper in the container under a force of a compressed spring.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1 shows an exemplary embodiment of a medicament delivery device with a delivery initiation indicator according to the present invention before use, FIG. 2 shows an exemplary embodiment of a medicament delivery device with a delivery initiation indicator according to the present invention during use;

FIG. 3 shows an exemplary embodiment of a medicament delivery device with a delivery initiation indicator according to the present invention during use;

FIG. 4 shows an exemplary embodiment of a medicament delivery device with a delivery initiation indicator according to the present invention during use;

FIG. 5 shows an exemplary embodiment of a medicament delivery device with a delivery initiation indicator according to the present invention after use;

Corresponding parts are marked with the same reference symbols in all figures.

DETAILED DESCRIPTION

Figure 6A:
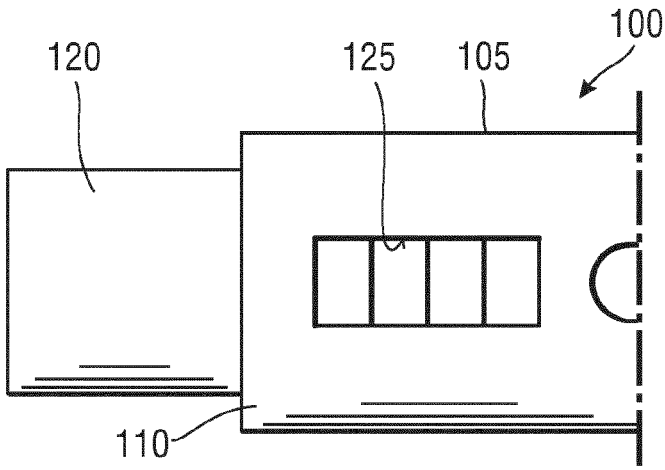
FIGS. 6A-E show exemplary embodiments a delivery initiation indicator according to the present invention.

FIG. 1 shows an exemplary embodiment of a medicament delivery device 100 according to the present invention. The delivery device 100 may be any type of injection device which is used to inject a medicament from a syringe or cartridge. Those of skill in the art will understand that such injection devices include, but are not limited to, pen injectors, pre-filled syringes, autoinjectors, perfusion devices, infusion devices, etc.

In the exemplary embodiment shown in FIG. 1, the delivery device 100 includes a case 105 which may be a cylinder having an open distal end 110 and a closed proximal end 115. Telescopically coupled to the case 105 may be a needle sleeve 120. The needle sleeve 120 may be biased (e.g., by a spring) in an extended position relative to the case 105 to ensure that a needle 300 on a syringe or cartridge in the delivery device 100 is covered prior to use.

In an exemplary embodiment, the case 105 includes a delivery initiation indicator (e.g., a first window 125) and delivery completion indicator (e.g., a second window 130). In the exemplary embodiment shown in FIG. 1, the first window 125 and the second window 130 are axially aligned on a longitudinal axis L of the delivery device 100, and the first window 125 is distal of the second window 130. However, those of skill in the art will understand that the windows 125, 130 may be axially and/or radially offset and arranged in any axial order (e.g., the first window 125 may be proximal of the second window 130).

In an exemplary embodiment, the windows 125, 130 are cut-outs in the case 125 (or molded voids) which contain a transparent cover. In another exemplary embodiment, the windows 125, 130 may not include the transparent cover.

FIG. 1 shows an exemplary embodiment of the delivery device 100 prior to use. FIG. 2 shows an exemplary embodiment of the delivery device 100 during use, when the delivery device 100 has been placed on an injection site. As the delivery device 100 is placed on the injection site, a distal end of the needle sleeve 120 contacts the injection site, and continued distally directed force causing the needle sleeve 120 to move in the proximal direction relative to the case 105 against the biasing force. As the needle sleeve 120 moves proximally, a portion of the needle sleeve 120 becomes visible in the first window 125.

FIG. 3 shows an exemplary embodiment of the delivery device 100 during use, when the needle sleeve 120 has moved into a retracted position relative to the case 105. In an exemplary embodiment, the needle sleeve is biased in the extended position by a spring 302. When the needle sleeve 120 is in the retracted position a distal end of a needle 300 may be exposed for insertion into the injection site, and an interlock mechanism 304 may be activated which advances a plunger 400 (under force of a compressed spring 306) into the syringe or cartridge to drive a stopper distally for expelling the medicament. In another exemplary embodiment, when the needle sleeve 120 has moved into the retracted position relative to the case 105, an interlock mechanism 304 may be activated which advances the syringe or cartridge from a first proximal position to a second distal position for inserting the needle 300 into the injection site. The interlock mechanism 304 may also cause advancement of the plunger 400 into the syringe or cartridge to drive the stopper distally for expelling the medicament, or a trigger button may be pressed to release the plunger 400.

A visual feedback is provided to the patient based on advancement of the needle sleeve 120 relative to the first window 125. That is, the patient may know that the needle 300 will be inserted or that an injection will begin (e.g., the plunger 400 will be released) when the needle sleeve 120 occupies the visual area (e.g., axial area) of the first window 125.

FIG. 4 shows an exemplary embodiment of the delivery device 100 during use, when the medicament has been delivered. The needle sleeve 120 has occupies a visual area of the first window 125 and the plunger 400 (by advancing through the syringe or cartridge) occupies a visual area of the second window 130. The visual presence of the plunger 400 in the second window 130 provides a visual feedback that an injection is complete.

FIG. 5 shows an exemplary embodiment of the delivery device 100 after use, when the delivery device 100 has been removed from the injection site. Under the biasing force, the needle sleeve 120 returns to the extended position relative to the case 105.

In an exemplary embodiment, the needle sleeve 120 may be locked in the extended position to prevent reused of the delivery device 100.

Figure 6B:
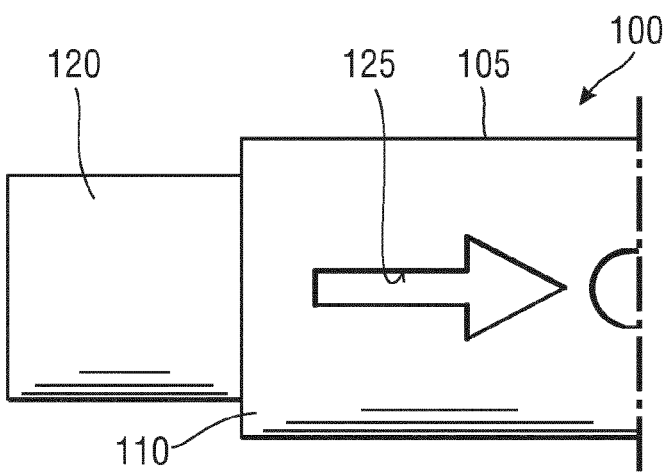
Figure 6C:
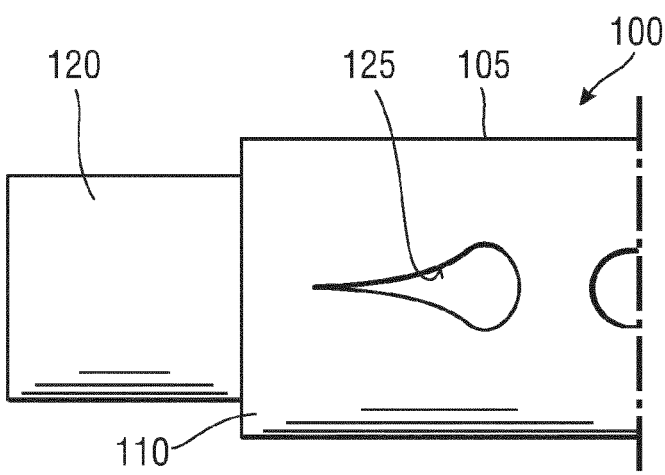
Figure 6D:
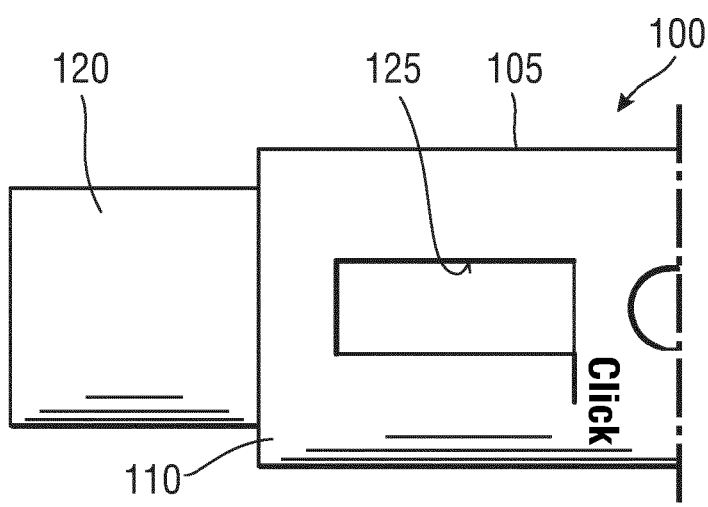
Figure 6E:
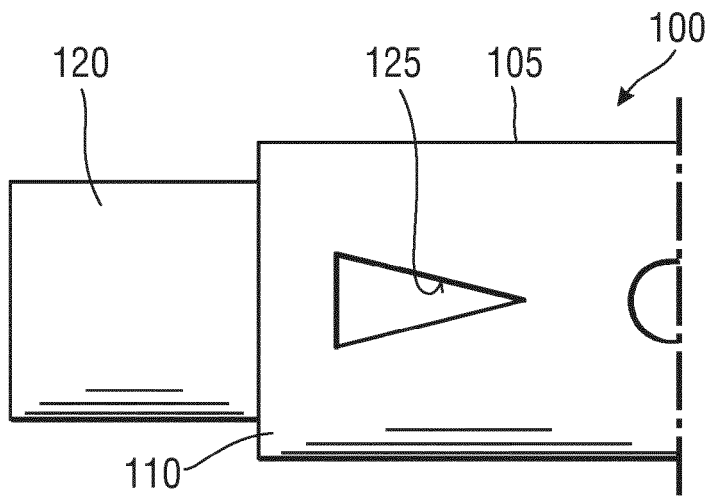

While the exemplary embodiments of the delivery device 100 shown in FIGS. 1-5 depict the first window 125 as being rectangular, those of skill in the art will understand that various shapes and/or indicia may be used for the delivery initiation indicator. For example, FIG. 6A shows the first window 125 including a plurality of transverse lines which may be equidistant apart or have decreasing spacing from a distal to a proximal end. FIG. 6B shows the first window 125 shaped as an arrow which may be oriented to point toward the proximal end 115 or the distal end 110 of the case 105. FIG. 6C shows the first window 125 having a droplet shape which may be oriented to point toward the proximal end 115 or the distal end 110 of the case 105. FIG. 6D shows the first window 125 having a text indicia, e.g., the word "Click". FIG. 6E shows the first window 125 shaped as a triangle which may be oriented to point toward the proximal end 115 or the distal end 110 of the case 105. Those of skill in the art will understand that any combination of the first window 125 and indicia (e.g., shape, color, text, graphics) may be utilized as the delivery initiation indicator, and the delivery initiation indicator may be disposed on the first window 125, on the case 105 adjacent the first window 125 or on a portion of the needle sleeve 120 such that it is visible through the first window 125 as the needle sleeve 120 moves from the extended position to the retracted position.

Figure 7:
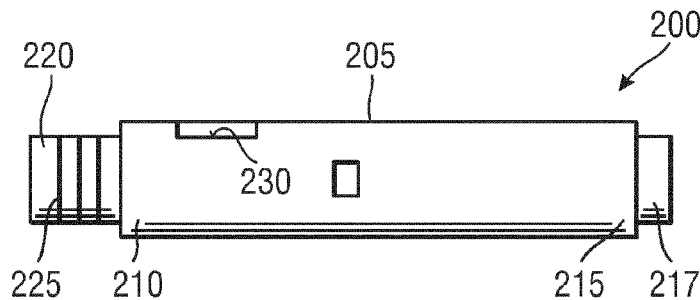
FIG. 7 shows another exemplary embodiment of a medicament delivery device with a delivery initiation indicator according to the present invention before use.

FIG. 7 shows another exemplary embodiment of a medicament delivery device 200 according to the present invention. The delivery device 200 may be any type of injection device which is used to inject a medicament from a syringe or cartridge. Those of skill in the art will understand that such injection devices include, but are not limited to, pen injectors, pre-filled syringes, autoinjectors, perfusion devices, infusion devices, etc.

In the exemplary embodiment shown in FIG. 7, the delivery device 200 includes a case 205 which may be a cylinder having an open distal end 210 and a proximal end 215. A trigger button 217 may be coupled to the proximal end 215 of the case 205. Telescopically coupled to the case 205 may be a needle sleeve 220. The needle sleeve 220 may be biased (e.g., by a spring) in an extended position relative to the case 205 to ensure that a needle 300 on a syringe or cartridge in the delivery device 200 is covered prior to use.

In an exemplary embodiment, the case 205 includes a delivery initiation indicator (e.g., an indicia 225) and delivery completion indicator (e.g., a window 230). In the exemplary embodiment shown in FIG. 7, the indicia 225 include a series of circumferential lines formed on a distal end of the needle sleeve 220. The lines may be equidistant apart or have decreasing spacing from a distal to a proximal end. In the extended position of the needle sleeve 220, an entirety of the indicia 225 (e.g., all of the lines) may be visible.

Figure 8:
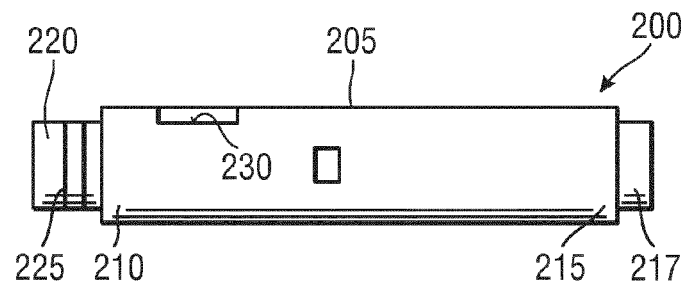
FIG. 8 shows another exemplary embodiment of a medicament delivery device with a delivery initiation indicator according to the present invention during use.

FIG. 7 shows an exemplary embodiment of the delivery device 200 prior to use. FIG. 8 shows an exemplary embodiment of the delivery device 200 during use, when the delivery device 200 has been placed on an injection site. As the delivery device 200 is placed on the injection site, a distal end of the needle sleeve 220 contacts the injection site, and continued distally directed force causes the needle sleeve 220 to move in the proximal direction relative to the case 205 against the biasing force. As the needle sleeve 220 moves proximally, a portion of the indicia 225 is covered by the distal end of the case 205.

Figure 9:
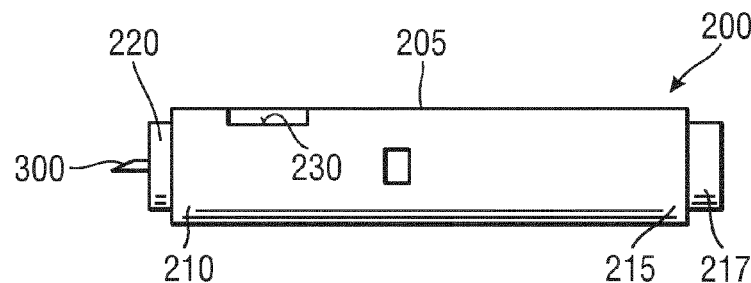
FIG. 9 shows another exemplary embodiment of a medicament delivery device with a delivery initiation indicator according to the present invention during use.

FIG. 9 shows an exemplary embodiment of the delivery device 200 during use, when the needle sleeve 220 has moved into a retracted position relative to the case 205. In an exemplary embodiment, when the needle sleeve 220 is in the retracted position a distal end of a needle 300 may be exposed for insertion into the injection site or an interlock mechanism may be activated which advances the syringe or cartridge from a first proximal position to a second distal position for inserting the needle 300 into the injection site. Whether the needle 300 is manually inserted or automatically inserted, when the trigger button 217 is pressed, the plunger 400 may be released and advance (under the force of a compressed spring) into the syringe or cartridge to drive the stopper distally for expelling the medicament.

A visual feedback is provided to the patient based on advancement of the needle sleeve 220 relative to the case 205. That is, the patient may know that the needle 300 will be inserted when the indicia 225 are no longer visible.

Figure 10:
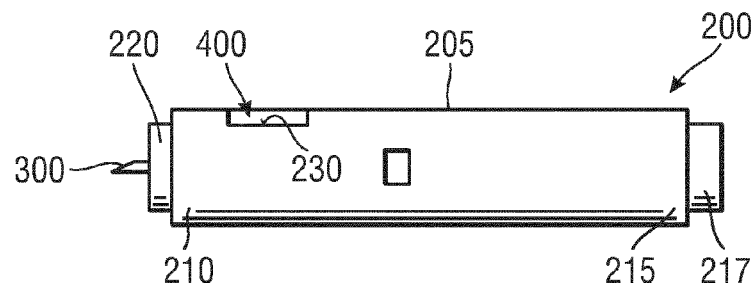
FIG. 10 shows another exemplary embodiment of a medicament delivery device with a delivery initiation indicator according to the present invention during use.

FIG. 10 shows an exemplary embodiment of the delivery device 200 during use, when the medicament has been delivered. The indicia 225 are covered by the case 205 and the plunger 400 (by advancing through the syringe or cartridge) occupies a visual area of the window 230. The visual presence of the plunger 400 in the window 230 provides a visual feedback that an injection is complete.

Figure 11:
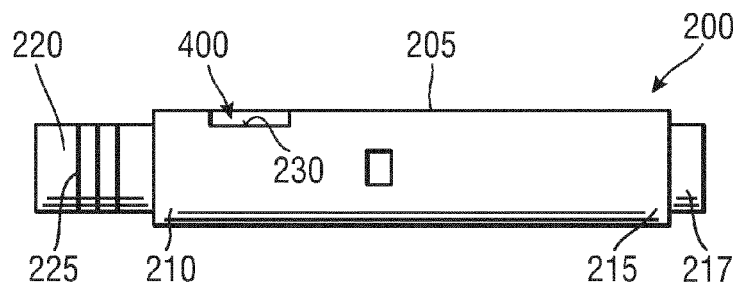
FIG. 11 shows another exemplary embodiment of a medicament delivery device with a delivery initiation indicator according to the present invention after use.

FIG. 11 shows an exemplary embodiment of the delivery device 200 after use, when the delivery device 200 has been removed from the injection site. Under the biasing force, the needle sleeve 220 returns to the extended position relative to the case 205. In an exemplary embodiment, the needle sleeve 220 may be locked in the extended position to prevent reused of the delivery device 200.

Figure 12A:
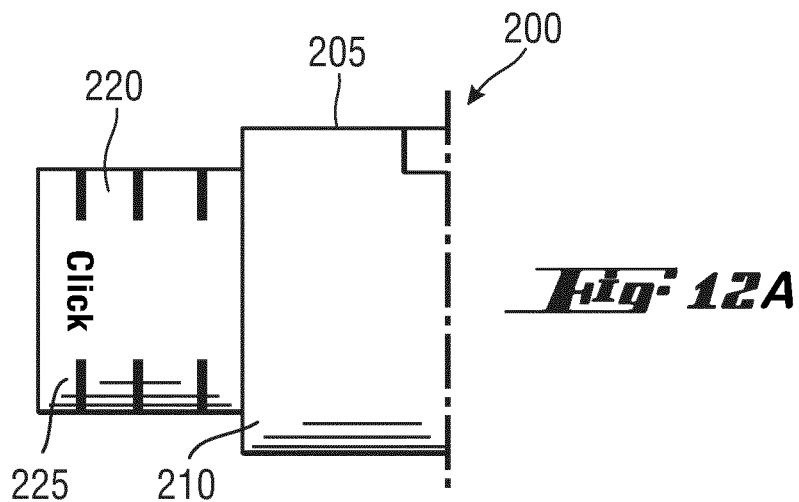
FIGS. 12A-C show exemplary embodiments a delivery initiation indicator according to the present invention.
Figure 12B:
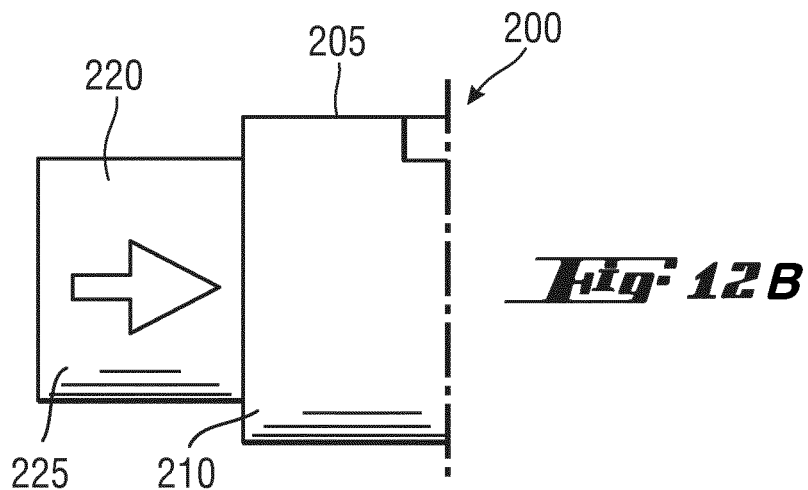
Figure 12C:
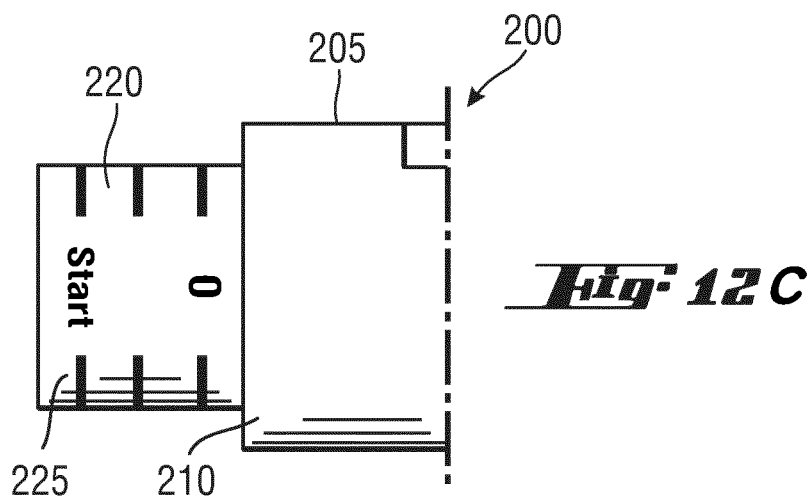

While the exemplary embodiments of the delivery device 200 shown in FIGS. 7-11 depict the indicia 225 as being a plurality of circumferential lines, those of skill in the art will understand that indicia (e.g., lines, text, graphics, shapes, etc.) may be used for the delivery initiation indicator. For example, FIG. 12A shows the indicia 225 as being a series of partially circumferential lines with a distal most partially circumferential line including a word (e.g., "click"). FIG. 12B shows the indicia 225 shaped as an arrow which may be oriented to point toward the proximal end 215 or the distal end 210 of the case 205. FIG. 12C shows the indicia 225 as being a series of partially circumferential lines with a proximal most circumferential line including a number (e.g., "0") and a distal most partially circumferential line including a word (e.g., "start"). Those of skill in the art will understand that any combination (e.g., shape, color, text, graphics) may be utilized as the delivery initiation indicator.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A medicament delivery device comprising:
    a case adapted to hold a container with a medicament, the container including a needle;
    a needle sleeve telescopically coupled to the case, the needle sleeve having an extended position relative to the case in which the needle is covered and a retracted position relative to the case in which the needle is exposed;
    a delivery initiation indicator formed in the case as a first window to provide a visual feedback of an initiation of a delivery of the medicament when the needle sleeve is in the retracted position;
    a second window formed in the case longitudinally offset from the first window which shows a portion of a plunger after delivery of the medicament, wherein the first window is distal to the second window; and
    an interlock mechanism operably coupled to the needle sleeve and adapted to release the plunger to push a stopper in the container under the force of a compressed spring.

2. The medicament delivery device according to claim 1, further including:
    a spring biasing the needle sleeve in the extended position.

3. The medicament delivery device according to claim 1, wherein the delivery initiation indicator shows an increasing portion of the needle sleeve when the needle sleeve moves from the extended position to the retracted position.

4. The medicament delivery device according to claim 3, wherein the increasing portion of the needle sleeve occupies a full visual area of the first window when the needle sleeve is in the retracted position.

5. The medicament delivery device according to claim 3, wherein the first window has a shape of a rectangle, a droplet, a triangle or an arrow.

6. The medicament delivery device according to claim 3, wherein an indicia is disposed on the first window, on the case or on a portion of the needle sleeve that is visible through the first window as the needle sleeve moves from the extended position to the retracted position.

7. The medicament delivery device according to claim 6, wherein the indicia includes one or more words, symbols, numbers, colors or lines.

8. The medicament delivery device according to claim 1, wherein the delivery initiation indicator is an indicia formed on the needle sleeve.

9. The medicament delivery device according to claim 8, wherein the indicia includes one or more words, symbols, numbers, colors or lines.

10. The medicament delivery device according to claim 8, wherein the indicia is covered by the case when the needle sleeve is in the retracted position.

11. The medicament delivery device according to claim 8, further comprising a window formed in the case which shows a portion of a plunger after delivery of the medicament.

12. The medicament delivery device according to claim 11, further comprising:
 a trigger button coupled to the case and operably coupled to the plunger; and
 wherein the trigger button is configured to release the plunger to push the stopper in the container under the force of the compressed spring.

13. A medicament delivery device comprising:
 a case adapted to hold a container with a medicament, the container including a needle;
 a needle sleeve telescopically coupled to the case, the needle sleeve moveable between an extended position relative to the case in which the needle is covered and a retracted position relative to the case in which the needle is exposed, wherein a delivery of the medicament is initiated in response to the needle sleeve moving from the extended position to the retracted position;
 a delivery initiation indicator formed in the case, the delivery initiation indicator configured to provide a visual feedback of the initiation of the delivery of the medicament in response to the needle sleeve moving from the extended position to the retracted position, the delivery initiation indicator comprising:
  a first window formed in the case and through which the movement of the needle sleeve from the extended position to the retracted position is visible, wherein the delivery completion indicator comprises a second window formed in the case adjacent the first window and longitudinally offset from the first window, the second window configured to show a portion of a plunger driven to deliver the medicament, wherein the first window is distal to the second window; and
 an interlock mechanism operably coupled to the needle sleeve, wherein activating the interlock mechanism enables advancement of the plunger to deliver the medicament, and wherein, upon delivery of the medicament, the plunger occupies the entire second window.

14. The medicament delivery device according to claim 13, wherein, in the retracted position, the needle sleeve occupies the entire first window.

15. The medicament delivery device according to claim 13, wherein the medicament delivery device comprises a delivery completion indicator formed in the case, the delivery completion indicator configured to provide a visual feedback of a completion of the delivery of the medicament.

16. The medicament delivery device according to claim 1, wherein the first window and the second window are offset from each other along a longitudinal axis of the case.

* * * * *